(12) United States Patent
Besser et al.

(10) Patent No.: US 10,350,145 B2
(45) Date of Patent: *Jul. 16, 2019

(54) NASOGASTRIC TUBE

(71) Applicant: ENVIZION MEDICAL LTD., Tel Aviv (IL)

(72) Inventors: Doron Besser, Tel Aviv (IL); Guy Ben Ezra, Karkur (IL)

(73) Assignee: ENVIZION MEDICAL LTD., Tel Aviv (IL)

( * ) Notice: Subject to any disclaimer, the term of this patent is extended or adjusted under 35 U.S.C. 154(b) by 357 days.

This patent is subject to a terminal disclaimer.

(21) Appl. No.: 15/044,162

(22) Filed: Feb. 16, 2016

(65) Prior Publication Data

US 2016/0158111 A1    Jun. 9, 2016

Related U.S. Application Data

(63) Continuation-in-part of application No. 14/098,426, filed on Dec. 5, 2013, now Pat. No. 9,789,029, which
(Continued)

(51) Int. Cl.
*A61J 15/00* (2006.01)
*A61M 16/04* (2006.01)

(52) U.S. Cl.
CPC ......... *A61J 15/0073* (2013.01); *A61J 15/003* (2013.01); *A61J 15/0003* (2013.01); *A61M 16/04* (2013.01); *A61M 16/0465* (2013.01); *A61M 16/0475* (2014.02); *A61M 16/0477* (2014.02); *A61M 16/0479* (2014.02); *A61M 16/0484* (2014.02); *A61M 16/0486* (2014.02); *A61M 16/0409* (2014.02); *A61M 2210/1032* (2013.01)

(58) Field of Classification Search
CPC .. A61B 5/05; A61B 5/06; A61B 5/061; A61B 5/062; A61M 16/04; A61M 16/0402; A61M 16/0409; A61M 2210/1032; A61M 16/0465; A61M 16/0472; A61M 16/0475; A61M 16/0477; A61M 16/0479; A61M 16/0481; A61M 16/0484; A61M 16/0486; A61M 16/0461; A61J 15/0073; A61J 15/0003; A61J 15/003
See application file for complete search history.

(56) References Cited

U.S. PATENT DOCUMENTS 4,904,238 A    2/1990   Williams
4,968,307 A   11/1990   Dake et al.
(Continued)

FOREIGN PATENT DOCUMENTS

EP    2301512         9/2009
EP    2301512 A2 *   3/2011   ............ A61J 15/003
(Continued)

*Primary Examiner* — Bhisma Mehta
*Assistant Examiner* — William R Frehe
(74) *Attorney, Agent, or Firm* — The Roy Gross Law Firm, LLC; Roy Gross

(57) ABSTRACT

A system comprising a nasogastric tube comprising a nasogastric location element, a feeding mechanism, a suction mechanism configured to sealingly draw an inner wall of an esophagus against said nasogastric tube, and a gastric decompression mechanism.

18 Claims, 6 Drawing Sheets

Related U.S. Application Data is a continuation-in-part of application No. 13/982,289, filed as application No. PCT/US2012/046850 on Jul. 16, 2012, now Pat. No. 9,839,584.

(60) Provisional application No. 62/185,941, filed on Jun. 29, 2015, provisional application No. 61/508,670, filed on Jul. 17, 2011.

(56) References Cited

U.S. PATENT DOCUMENTS

| | | | |
|---|---|---|---|
| 5,389,074 A | 2/1995 | Parker et al. | |
| 5,707,351 A | 1/1998 | Dorsey, III | |
| 6,126,647 A * | 10/2000 | Posey | A61M 25/0127 |
| | | | 600/12 |
| 6,165,164 A * | 12/2000 | Hill | A61B 18/1492 |
| | | | 604/523 |
| 6,695,764 B2 * | 2/2004 | Silverman | A61F 2/04 |
| | | | 600/29 |
| 6,790,214 B2 | 9/2004 | Kraemer et al. | |
| 7,794,425 B2 | 9/2010 | Gobel | |
| 7,967,780 B2 | 6/2011 | Goebel | |
| 8,100,874 B1 | 1/2012 | Jordan et al. | |
| 8,453,648 B2 * | 6/2013 | Black | A61M 16/0486 |
| | | | 128/205.24 |
| 9,789,029 B2 * | 10/2017 | Besser | A61J 15/003 |
| 2003/0208209 A1 | 11/2003 | Gambale et al. | |
| 2004/0082909 A1 | 4/2004 | Shia et al. | |
| 2004/0153098 A1 * | 8/2004 | Chin | A61B 17/00008 |
| | | | 606/129 |
| 2004/0220515 A1 | 11/2004 | Constantz | |
| 2005/0059962 A1 | 3/2005 | Phan et al. | |
| 2005/0137574 A1 | 6/2005 | Sakal et al. | |
| 2008/0077043 A1 | 3/2008 | Malbrain et al. | |
| 2008/0195047 A1 | 8/2008 | Price | |
| 2009/0069796 A1 | 3/2009 | Oskin | |
| 2009/0306626 A1 | 12/2009 | Sinha et al. | |
| 2009/0317760 A1 * | 12/2009 | Gadbois | A61C 17/043 |
| | | | 433/91 |
| 2010/0030133 A1 | 2/2010 | Elia et al. | |
| 2011/0046653 A1 | 2/2011 | Addington et al. | |
| 2011/0130650 A1 | 6/2011 | Dayan et al. | |
| 2012/0150111 A1 | 6/2012 | Hershey et al. | |
| 2013/0158471 A1 | 6/2013 | Neel et al. | |
| 2013/0310806 A1 | 11/2013 | Nevler et al. | |
| 2014/0066880 A1 | 3/2014 | Prince et al. | |
| 2014/0088359 A1 | 3/2014 | Quaye | |
| 2014/0100531 A1 | 4/2014 | Ankrum et al. | |
| 2014/0188080 A1 | 7/2014 | Besser et al. | |
| 2014/0235960 A1 | 8/2014 | Addington et al. | |
| 2015/0174013 A1 | 6/2015 | Besser et al. | |

FOREIGN PATENT DOCUMENTS

| | | | |
|---|---|---|---|
| EP | 2301512 A2 * | 3/2011 | A61J 15/003 |
| WO | 2003034976 | 5/2003 | |
| WO | 2007095541 | 8/2007 | |
| WO | 2013012774 | 1/2013 | |
| WO | 2015198297 | 11/2015 | |
| WO | 2016024260 | 2/2016 | |

* cited by examiner

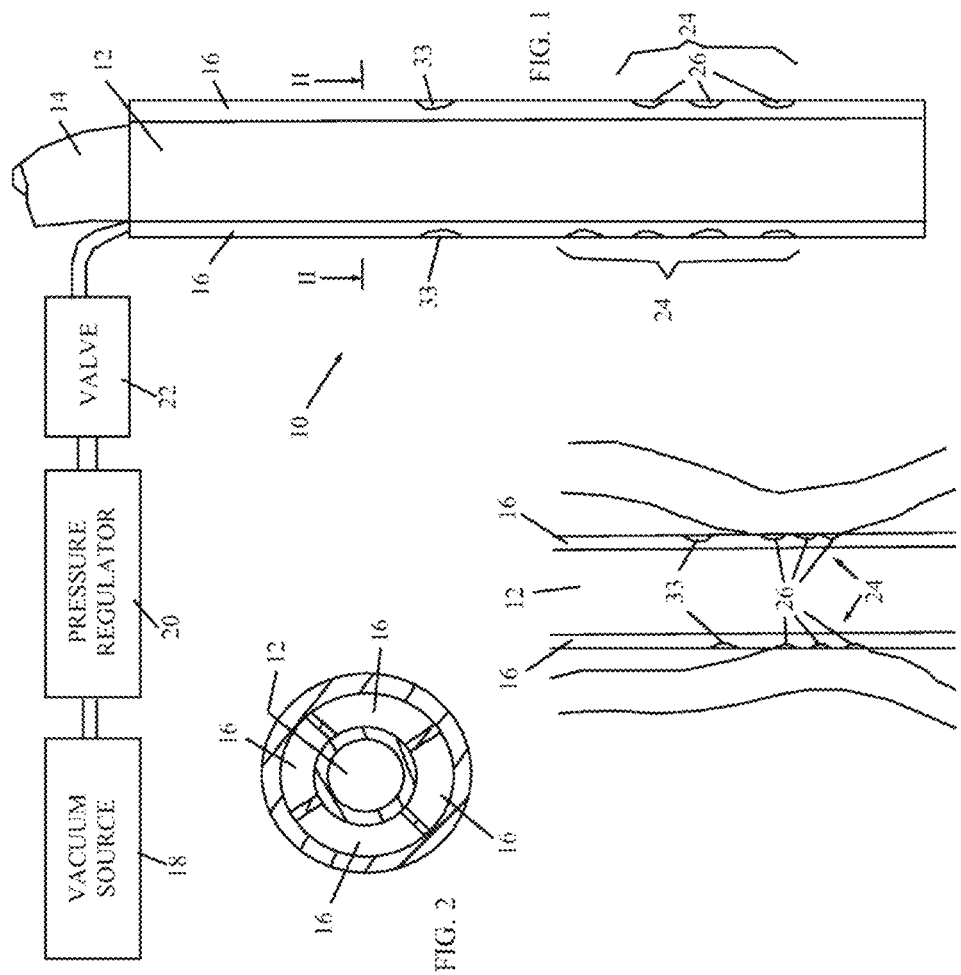

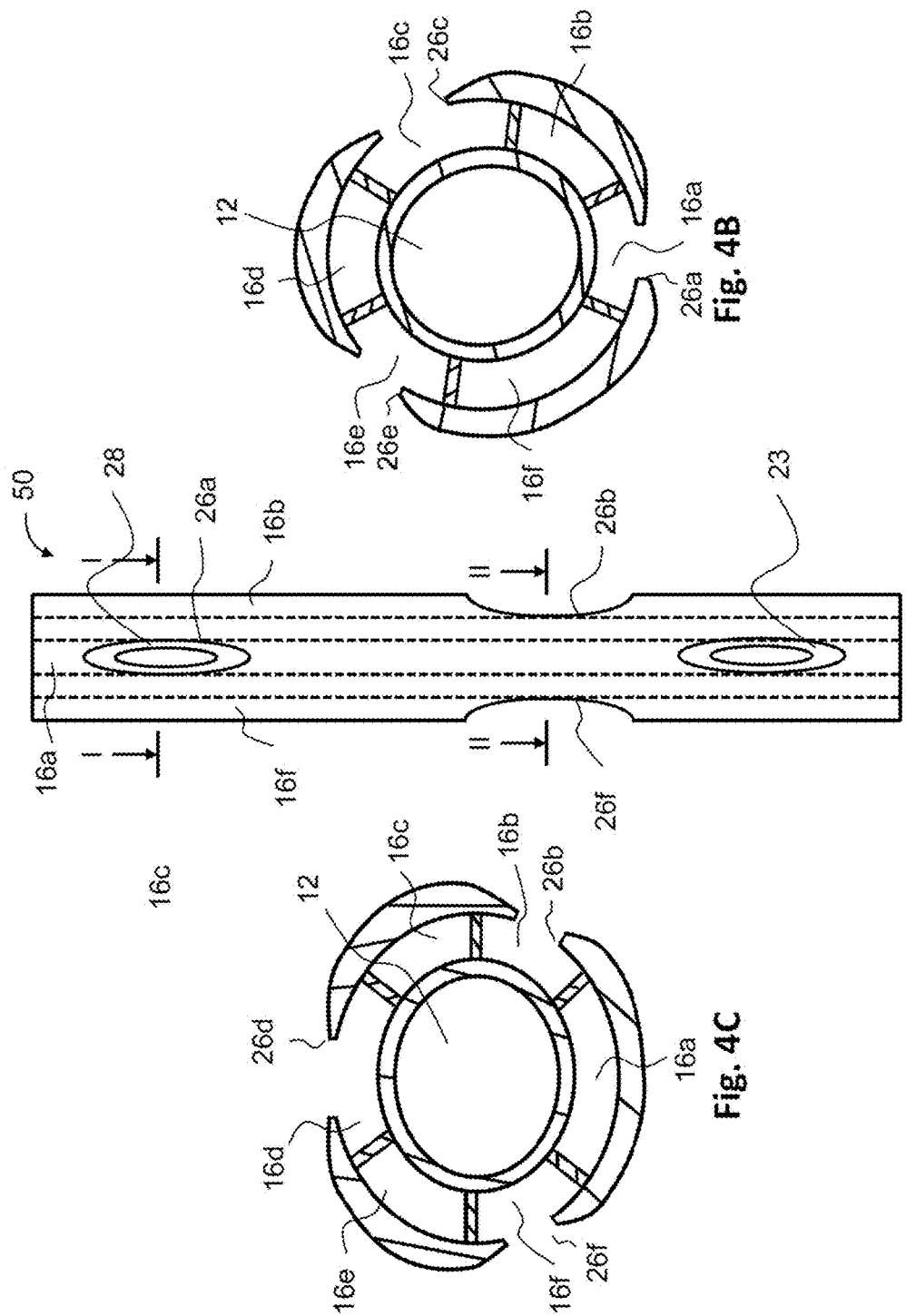

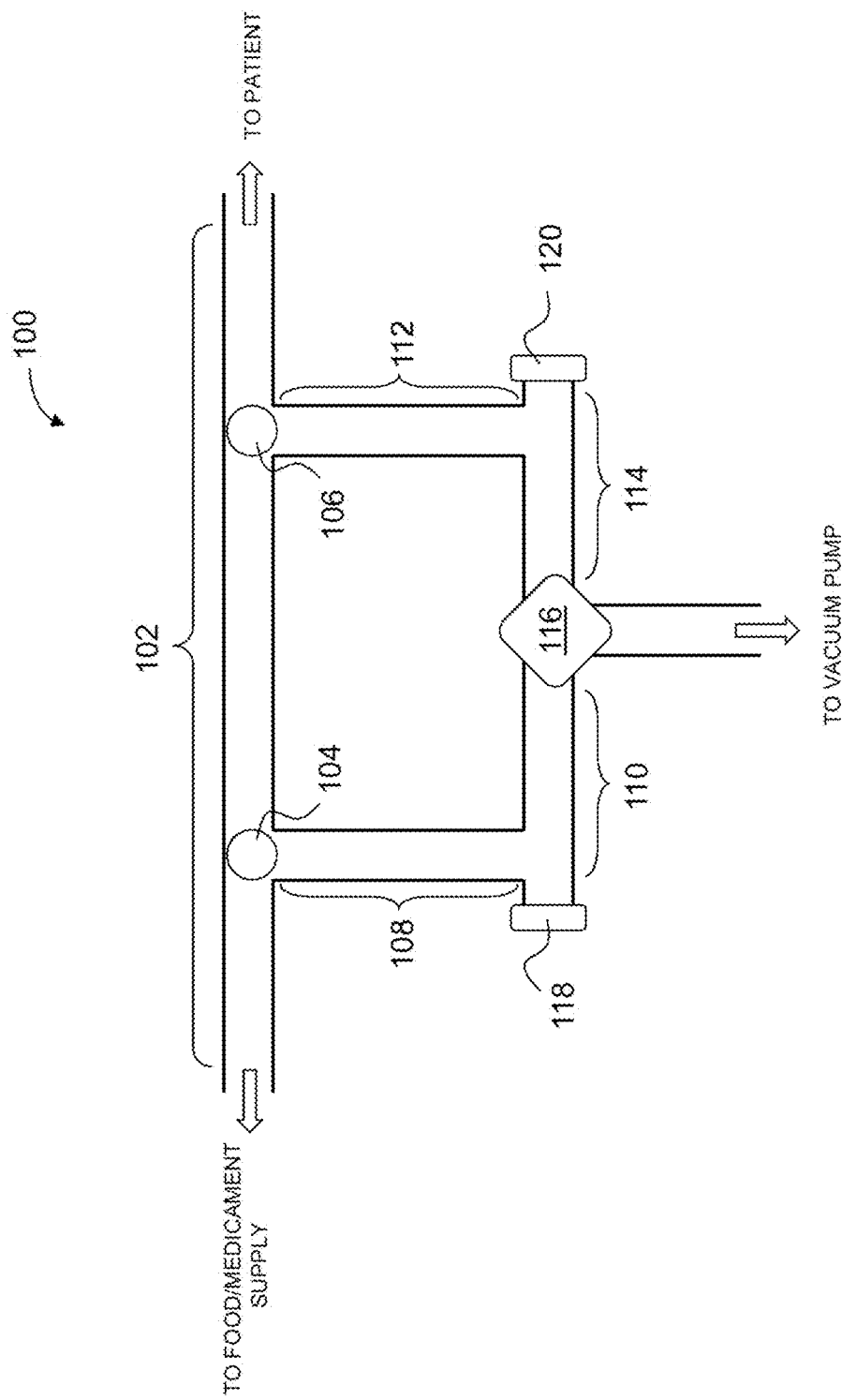

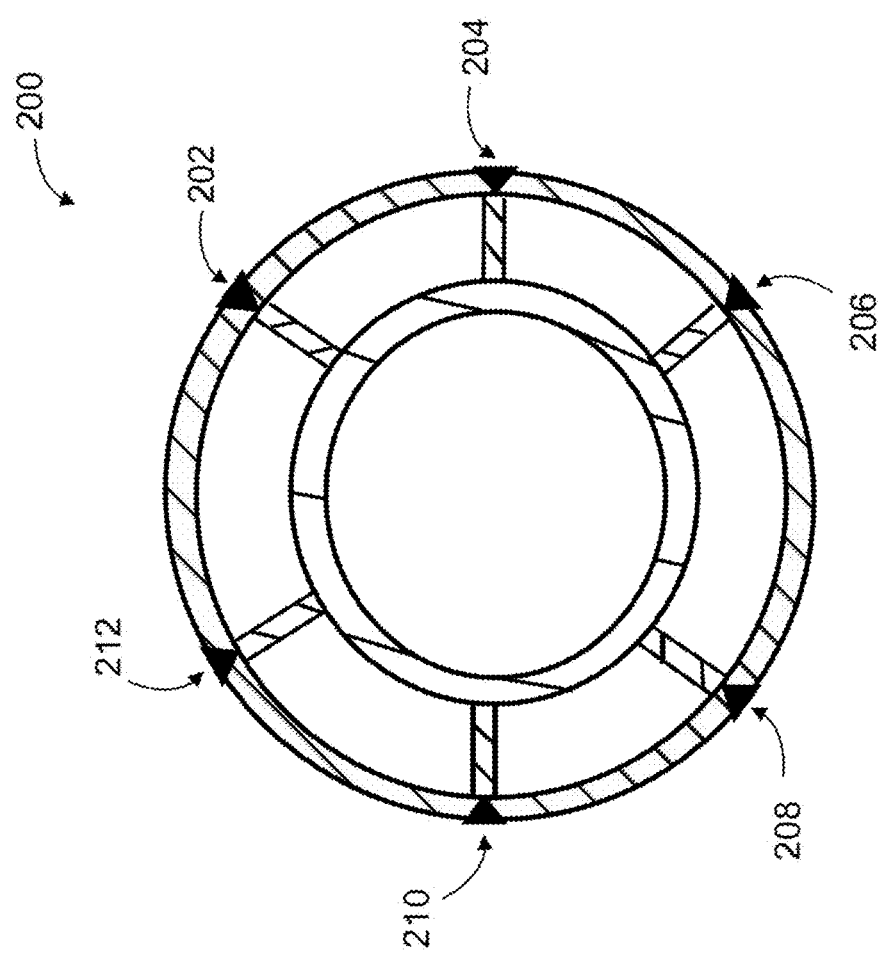

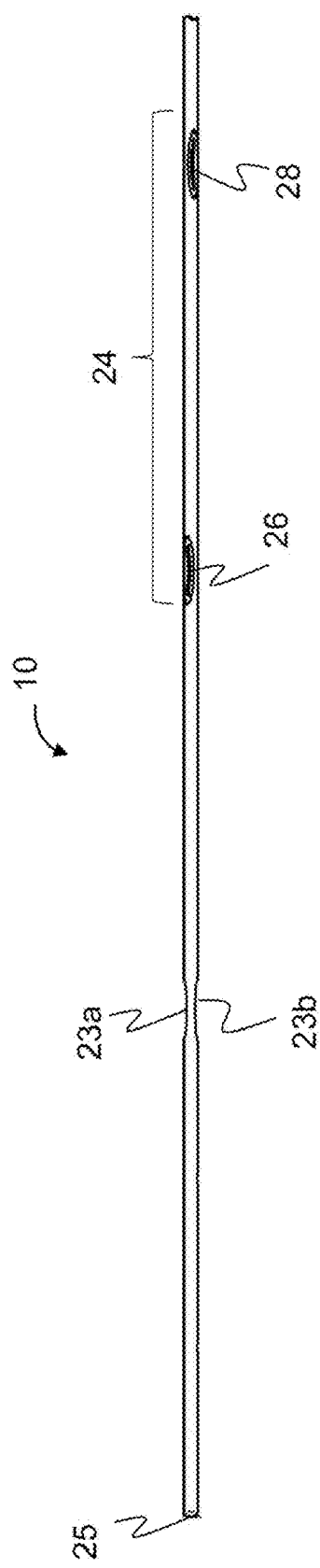
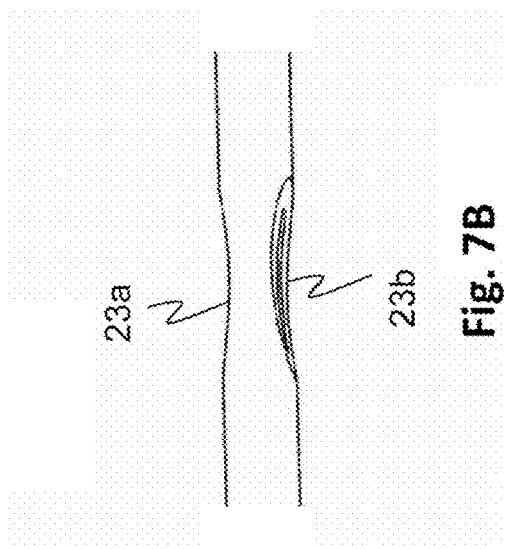
Fig. 7A
Fig. 7B

NASOGASTRIC TUBE

CROSS-REFERENCE TO RELATED APPLICATION

This application claims priority to and the benefit of U.S. Provisional Application No. 62/185,941 filed 29 Jun. 2015, and is a continuation in part of U.S. application Ser. No. 14/098,426 filed 5 Dec. 2013 and is a continuation in part of U.S. application Ser. No. 13/982,289, filed 29 Jul. 2013. The entire contents of all of these are incorporated herein by reference.

FIELD OF THE INVENTION

The present invention relates generally to a nasogastric location element imbedded in a nasogastric tube.

BACKGROUND

Enteral feeding is a form of hyperalimentation and metabolic support in which nutrient formulas or medicaments are delivered directly to the GI tract, either to the stomach or the duodenum. A nasogastric tube (NGT) is used for feeding and administering drugs and other oral agents. The tube is inserted into the patient's esophagus and stomach in order to ensure the passage of the agents into the stomach and not into the lungs. The NGT can also be used for suction of fluids from the stomach.

However, the use of NGTs can have disadvantages. Minor complications include nose bleeds, sinusitis, and a sore throat. Sometimes more significant complications occur including erosion of the nose where the tube is anchored, esophageal perforation, pulmonary aspiration, a collapsed lung, or intracranial placement of the tube.

Even worse, during feeding, excessive gastric pressure may result. From time to time, the body relieves such excess gastric pressure by expelling gas or liquid or reflux fluid. The fluids are expelled from the stomach through the esophagus to the mouth or nasal pathways. The reflux fluids may be inhaled into the lungs with possible risk of aspiration pneumonia, bacterial infection in the pharynx or esophagus or any other ailments. Accordingly, numerous studies have linked the use of the NGT to an increase in ventilator-associated pneumonia (VAP). VAP is the most common nosocomial infection in the intensive care unit (ICU), and it is associated with prolonged hospitalization, increased health care costs, and high attributable mortality.

US Patent Application Publication No. 2013/0310806 provides a nasogastric tube including a main lumen having one or more proximal connectors for connecting to a source of substances or pressure, and one or more vacuum lumens peripherally surrounding the main lumen, each vacuum lumen including a vacuum sealing portion which includes one or more suction ports for sealingly drawing an inner wall of an esophagus thereagainst.

There exists a pressing need for an NGT that is capable of significantly reducing the risk of reflux food and developing VAP, as well as simultaneously removing excessive gastric gas by gastric decompression.

SUMMARY

The following embodiments and aspects thereof are described and illustrated in conjunction with systems, tools and methods which are meant to be exemplary and illustrative, not limiting in scope.

There is provided, in accordance with an embodiment, a system comprising a nasogastric tube comprising a feeding mechanism, a suction mechanism configured to sealingly draw an inner wall of an esophagus against said nasogastric tube, a nasogastric location element and possibly a gastric decompression mechanism and/or pump configured to draw a liquid from a reservoir to a nasogastric tube.

There is provided, in accordance with another embodiment, a system comprising: a nasogastric tube having a length and comprising: (a) a main lumen having one or more proximal connectors configured to connect to a source of substances or pressure; (b) at least two vacuum lumens peripherally surrounding said main lumen; (c) at least two suction ports configured to sealingly draw an inner wall of an esophagus thereagainst, each of said at least two suction ports associated with a different one of said at least two vacuum lumens, wherein said at least two suction ports are distributed between at least two different locations along the length of said nasogastric tube; and (d) a nasogastric location element. In addition the system may further comprise at least one gastric decompression port associated with at least one of said at least four vacuum lumens, said at least one gastric decompression port being disposed distally to the at least two different locations along the length of said nasogastric tube.

There is provided, in accordance with another embodiment, a system comprising a nasogastric tube having a length and comprising: (a) at least three lumens; (b) a main lumen having one or more proximal connectors configured to connect to a source of substances or pressure; (c) at least two suction ports each associated with a different one of at least three vacuum lumens peripherally surrounding a main lumen, said at least two suction ports are configured to sealingly draw an inner wall of an esophagus thereagainst, wherein said at two suction ports are distributed between at least two different locations along the length of said nasogastric tube; (d) at least one gastric decompression port associated with an additional at least one vacuum lumen, said at least one gastric decompression port being disposed distally to the at least two different locations along the length of said nasogastric tube; and (e) a nasogastric location element.

There is further provided, in accordance with an embodiment, a method for positioning a nasogastric tube in the esophagus of a patient, said nasogastric tube comprising a suction mechanism configured to sealingly draw an inner wall of an esophagus against said nasogastric tube, a nasogastric location element, and possibly a gastric decompression mechanism; applying vacuum so as to decompress gastric gas; and applying vacuum so as to sealingly draw an inner wall of an esophagus thereagainst.

There is further provided, in accordance with an embodiment, a method for positioning a nasogastric tube into an esophagus of a patient, said nasogastric tube having a length and comprising a main lumen having one or more proximal connectors for connecting to a source of substances or pressure, three or more vacuum lumens peripheral to said main lumen, two or more suction ports, each of said two or more suction ports associated with a different one of said three or more vacuum lumens, a nasogastric location element, and possibly at least one gastric decompression port being disposed distally to the at least two different locations along the length of said nasogastric tube; applying vacuum so as to decompress gastric gas; and applying vacuum interchangeably to said three or more vacuum lumens so as to sealingly draw an inner wall of an esophagus thereagainst, each time in a different location along said esophagus.

In some embodiments, a nasogastric location element is disposed within at least one vacuum lumen. In another embodiment, a nasogastric location element is disposed within at least one vacuum lumen which does not include a suction port.

In some embodiments, a nasogastric location element is disposed within the plastic wall of the main lumen or any one or more of the peripheral lumens.

In some embodiments, the method of the invention further comprises applying vacuum so as to aspirate fluids from the esophagus.

In some embodiments, the system further comprises a vacuum source connected to said vacuum lumens.

In some embodiments, said vacuum lumens are connected to a vacuum source via a pressure regulator and a valve.

In some embodiments, said main lumen and said vacuum lumens are constructed as one unit.

In some embodiments, said vacuum lumens are a separate unit from said main lumen, and wherein said vacuum lumens are slidable relative to said main lumen.

In some embodiments, said main lumen and said vacuum lumens are arranged as concentrically arranged conduits.

In some embodiments, the system further comprises one or more auxiliary suction ports proximal to said at least four suction ports.

In some embodiments, each of said at least four suction ports comprises a graduated edging.

In some embodiments, the system further comprises a manifold configured to connect said vacuum lumens to said valve.

In some embodiments, said manifold is transparent.

In some embodiments, said vacuum lumens comprise at least six vacuum lumens.

In some embodiments, at least one of said at least four suction ports comprises two or more suction ports, successively arranged along a portion of the length of said nasogastric tube.

In some embodiments, said nasogastric tube further comprises two or more longitudinal radiopaque stripes.

In some embodiments, said two or more longitudinal radiopaque stripes are embedded in an outer wall of said nasogastric tube.

In some embodiments, the method further comprises regulating the vacuum so that a suction level is not constant over time.

In some embodiments, the method further comprises regulating vacuum to said four or more suction ports of said four or more vacuum lumen, so as to create peristaltic movement or other oscillatory movement of the esophagus.

In some embodiments, said applying of the vacuum restricts at least 60% of passage through the esophagus.

In some embodiments, the method further comprises visually monitoring a transparent manifold coupling said four or more vacuum lumens with said valve for backflow of gastric substances.

In addition to the exemplary aspects and embodiments described above, further aspects and embodiments will become apparent by reference to the figures and by study of the following detailed description.

BRIEF DESCRIPTION OF THE DRAWINGS

The present invention will be understood and appreciated more fully from the following detailed description taken in conjunction with the drawings in which:

FIG. 1 is a simplified schematic illustration of a nasogastric tube, constructed and operative in accordance with a non-limiting embodiment of the present invention;

FIG. 2 is a simplified sectional illustration of the NGT of FIG. 1, taken along lines II-II in FIG. 1;

FIG. 3 is a simplified schematic illustration of the nasogastric tube being used to suck and seal the inner wall of the esophagus against the NGT, in accordance with an embodiment of the present invention;

FIG. 4A is a simplified, schematic illustration of a transparent front view of a portion of a nasogastric tube, constructed and operative in accordance with another embodiment of the present invention;

FIG. 4B is a simplified schematic illustration of a cross-section along line I-I of the nasogastric tube of FIG. 4A;

FIG. 4C is a simplified schematic illustration of a cross-section along line II-II of the nasogastric tube of FIG. 4A;

FIG. 5 is a schematic diagram of a manifold;

FIG. 6 is a cross section of a nasogastric tube;

FIG. 7A is a simplified, schematic illustration of a portion of a nasogastric tube in accordance with a non-limiting embodiment of the present invention; and FIG. 7B is a simplified enlarged illustration of a portion of the nasogastric tube comprising the decompression ports, in accordance with a non-limiting embodiment of the present invention.

DETAILED DESCRIPTION OF EMBODIMENTS

Figure 8A:
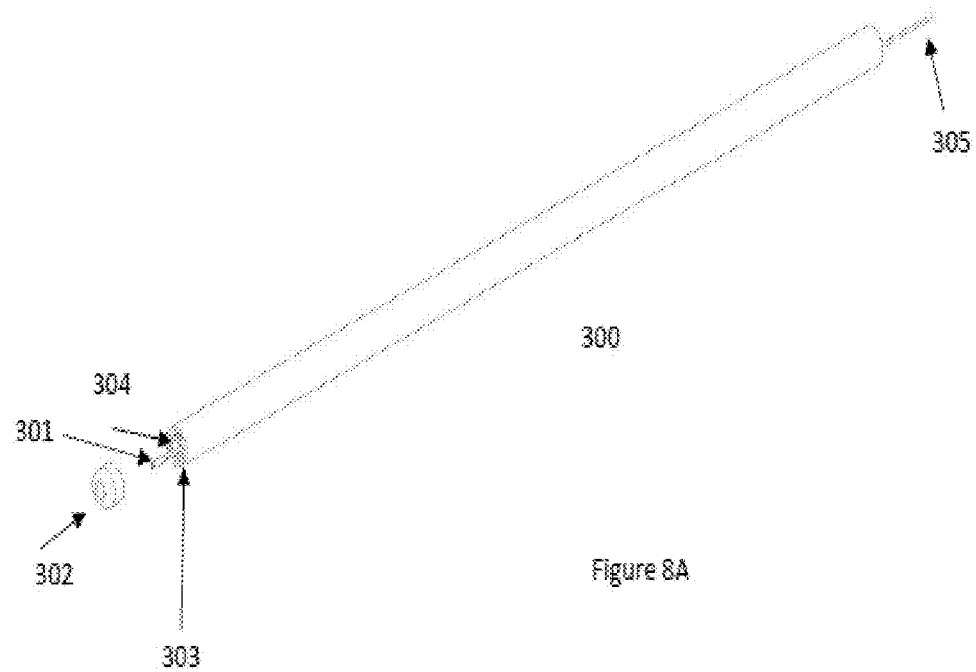
FIGS. 8A-B are simplified schematic illustrations of a nasogastric tube, constructed and operative in accordance with a non-limiting embodiment of the present invention.

The present invention provides a system comprising a nasogastric tube (NGT) comprising a nasogastric location element and a method thereof, as is described more in detail hereinbelow. A system as described herein includes an NGT having a nasogastric location element and a vacuum control unit. The vacuum control unit couples the esophagus to the tube thus disabling the reflux of the food along the esophagus to the trachea. Furthermore, the vacuum control unit enables decompression of a subject's abdomen, including but not limited to the stomach or intestines.

According to some embodiments, the NGT of the present invention is configured to be positioned and/or localized into a specific area of the esophagus and to perform as a feeding tube as well as a gastric decompression tube. Thus, the NGT enables administration of nutrients or drugs directly to a subject's stomach or intestines and simultaneously or interchangeably enables gastric decompression.

In accordance with an embodiment, the invention provides a system comprising an NGT coupled to a nasogastric location element. In accordance with an embodiment, the invention provides a method for determining the position of a nasogastric location element. In one embodiment, a nasogastric location element is a magnetic probe. In one embodiment, a nasogastric location element is detected by at least one magnetometer. In another embodiment, a system as described herein comprises an NGT coupled to a nasogastric location element and at least one magnetometer.

In another embodiment, a NGT as described herein is a nasogastric-enteral tube. In another embodiment, a NGT as described herein is an enteral tube. In another embodiment, a nasogastric location element comprises an enteral location element. In another embodiment, an enteral location element is located distally to the gastric portion of the NGT. In another embodiment, NGT includes both an enteral location element and a nasogastric location element. In another embodiment, a distal end of a NGT reaches the stomach. In another embodiment, a NGT occupies the esophagus. In another embodiment, a NGT which includes a nasoenteral tube (NET) further reaches at least one segment of the small intestines. In another embodiment, a NGT which includes a nasoenteral tube (NET) occupies a post pyloric segment.

In one embodiment, a NGT comprising a nasogastric location element is tracked by an electromagnetic tracking system. In another embodiment, a nasogastric location element comprises coils as transmitters, receivers, or both. In another embodiment, a nasogastric location element or a system comprising it is configured in an industry-standard coil architecture (ISCA). In another embodiment, a nasogastric location element or a system comprising it uses an array of six or more transmitter coils spread out in space and one or more quasi-dipole receiver coils. In another embodiment, a nasogastric location element or a system comprises an ISCA tracker architecture which uses a three-axis quasi-dipole coil transmitter and a three-axis quasi-dipole coil receiver.

In another embodiment, a system as described herein comprises: a transmitter and receiver wired to a common device or box. In another embodiment, a system as described herein is a wireless electromagnetic tracking system allowing for the NGT being tracked to move freely without being limited by connections with the transmitter or receiver. In another embodiment, a transponder is located within the NGT. In another embodiment, a transponder is located within a box placed near or on the patient, 2 to 30 cm from the NGT.

In one embodiment, a nasogastric location element is located at a predefined position within the NGT. In one embodiment, a nasogastric location element is a permanent magnet. In one embodiment, a nasogastric location element is an AC electromagnet. In one embodiment, a nasogastric location element is a cylinder to be fitted within a lumen as described herein.

In one embodiment, a nasogastric location element is a cylinder of 0.1 to 2 mm in diameter. In one embodiment, a nasogastric location element is a cylinder of 0.1 to 1 mm in diameter.

In one embodiment, a nasogastric location element is 0.1 to 6 mm long. In one embodiment, a nasogastric location element is 0.2 to 4 mm long. In one embodiment, a nasogastric location element is 0.4 to 3 mm long. In one embodiment, a nasogastric location element is 0.5 to 2 mm long.

In another embodiment, a nasogastric location element provides a magnetic signal that can be measured by at least one magnetometer. In another embodiment, a nasogastric location element is activated by a magnetic signal. In another embodiment, the magnetometers measure the three-dimensional magnetic field of the nasogastric location element, which can then be used to provide three-dimensional magnetic induction values.

In another embodiment, a nasogastric location element is connected or is a component within an electromagnetic tracking system. In another embodiment, an electromagnetic tracking system includes: a field generator, sensor unit and central control unit. In another embodiment, an electromagnetic tracking system includes: a field generator comprises coils to generate a position varying magnetic field that is used to establish the coordinate space. In another embodiment, a nasogastric location element comprises coils in which current is induced via the magnetic field. In another embodiment, the central control unit serves to control the field generator and capture data from the sensor unit.

In another embodiment, a field generator creates an electromagnetic field as the coordinates system—a set of wired sensor coils working within the reference field. In another embodiment, at each point inside the reference field, the coils (such as sensor coils) transfer back the field strength and orientation information through the signal wire. In another embodiment, this information is used to determine the position and posture of the sensor coils/NGT/nasogastric location element inside this field.

In another embodiment, a coil also referred to as a nasogastric location element used herein is small—such as the NDI Aurora coil. In another embodiment, tracking of NGT is wireless tracking with signal coils small enough to be implanted within the NGT's peripheral lumen (such as the Calypso product).

In another embodiment, an array of coils that induces a current by changing the magnetic field inside the working volume. In another embodiment, a system as described herein is based on Faraday's Law. In another embodiment, changes in the magnetic field result in a potential difference induced within the coil. In another embodiment, a measurable current is induced within the coils. In another embodiment, the magnitude of the voltage from the coil is proportional to the area circumscribed by the coil, the number of turns on the coil and the slew rate of the magnetic flux.

In another embodiment, a nasogastric location element provides magnetic gradient fields that can be superposed on the uniform magnetic field by means of gradient coil systems. In another embodiment, an RF transmitter generates an RF magnetic field in the examination zone, pulse-wise. In another embodiment, an RF transmitter generates an RF magnetic field in the esophageal and/or neck area, pulse-wise. In another embodiment, MR signals generated are detected by a receiving coil, in conjunction with a receiving device, and the nuclear magnetization distribution in the examination zone is reconstructed on the basis of the digitized MR signals, and the nuclear magnetization distribution is displayed as an MR image on a display unit.

In another embodiment, a nasogastric location element is a coil or a microcoil embedded within a lumen or within a lumen's wall. In another embodiment, the signals received by the nasogastric location element are applied to a receiving device so as to be digitized and for determining the position of the location element and superposes it on the MR image displayed on the display unit.

In another embodiment, a coil control unit controls the adjustment of the magnetic moment of the coil hen it is not switched to the receiving mode.

In some embodiments, a nasogastric location element receives a current via current leads. In another embodiment, a nasogastric location element is arranged in a lumen. In another embodiment, a nasogastric location element is arranged in a lumen free of a suction port. In another embodiment, pulling wires are connected so as to change the position of the nasogastric location element relative to the direction of the magnetic field.

In another embodiment, the NGT of the present invention, provides for the permanent presence of a nasogastric location element within the NGT, the location of the NGT or a portion thereof can be monitored at any time.

In another embodiment, imbedded into a lumen wall and/or placed within the lumen are a pair of flexible conductive leads. In another embodiment, imbedded into a lumen wall and/or placed within the lumen is a strip of radio-opaque material. In another embodiment, or placed within the lumen are a plurality of one way valve which is designed to prevent the back flow of fluids.

In another embodiment, a NGT as described herein comprises at least 2 vacuum lumens and at least one additional lumen housing the nasogastric location element. In another embodiment, a NGT as described herein comprises at least 3 peripheral lumens wherein at least 3 peripheral lumens include 2 vacuum lumens and an additional lumen housing the nasogastric location element. In another embodiment, a NGT as described herein is a 7 lumen extrusion with a dedicated lumen for the nasogastric location element. In another embodiment, the nasogastric location element is pre-assembled and then introduced into the lumen. In another embodiment, the NGT is a product of co-extrusion with the wires (within a lumen and/or imbedded into a wall of a lumen (any lumen)) and then assembling the nasogastric location element at the tip. In another embodiment, the nasogastric location element is located at the distal tip of the NGT. In another embodiment, the nasogastric location element is located anywhere along the distal to the proximal ends of the NGT. In another embodiment, the nasogastric location element is shaped as a stylet. In another embodiment, the nasogastric location element is a coil.

In another embodiment, provided herein a system for inserting, locating, and/or maneuvering a NGT in a patient in need thereof, wherein the system comprises a NGT as described herein and a system component for monitoring the location of the NGT. In another embodiment, the system component for monitoring the location of the NGT is placed outside of the patient's body. In another embodiment, the system component for monitoring the location of the NGT, comprises: a computerized processor; a display device operatively connected to the processor; a detector device operatively connected to the processor, the detector device being configured to be positioned over a predetermined location of a subject; a coil operatively connected to the processor, the coil being configured to be inserted into the NGT; a memory device storing: (a) a first predetermined line representative of a mid-sagittal line of a subject; (b) a second predetermined line representative of a chest anatomical structure such as but not limited to the diaphragm of the subject; and (c) instructions which when executed by the processor, cause the processor to, in cooperation with the display device, the detector device, the coil and the memory device, while the coil is being advanced or removed from the NGT: (a) display the first predetermined line representative of the mid-sagittal line of the subject and the predetermined line representative of the diaphragm of the subject; (b) for an esophageal segment, determine and display a first number indicative of a first distance from the coil to the detector device.

In another embodiment, the system component for monitoring the location of the NGT, comprises: a computerized processor; a display device operatively connected to the processor; a detector device operatively connected to the processor, the detector device being configured to be positioned over a predetermined location of a subject; a coil operatively connected to the processor, the coil being configured to be inserted into the NGT; a memory device storing: (a) a first predetermined line representative of a mid-sagittal line of a subject; (b) a second predetermined line representative of a chest anatomical structure such as but not limited to the diaphragm of the subject; and (c) instructions which when executed by the processor, cause the processor to, in cooperation with the display device, the detector device, the coil and the memory device, while the coil is being advanced or removed from the NGT: (a) display the first predetermined line representative of the mid-sagittal line of the subject and the predetermined line representative of the diaphragm of the subject; (b) for an esophageal segment, determine and display a first number indicative of a first distance from the coil to the detector device; and (c) for a stomach segment, determine and display a second number termine and display a third number indicative of a third distance from the coil to the indicative of a second distance from the coil to the detector device.

In another embodiment, the system component for monitoring the location of the NGT, comprises: a computerized processor; a display device operatively connected to the processor; a detector device operatively connected to the processor, the detector device being configured to be positioned over a predetermined location of a subject; a coil operatively connected to the processor, the coil being configured to be inserted into the NGT; a memory device storing: (a) a first predetermined line representative of a mid-sagittal line of a subject; (b) a second predetermined line representative of a chest anatomical structure such as but not limited to the diaphragm of the subject; and (c) instructions which when executed by the processor, cause the processor to, in cooperation with the display device, the detector device, the coil and the memory device, while the coil is being advanced or removed from the NGT: (a) display the first predetermined line representative of the mid-sagittal line of the subject and the predetermined line representative of the diaphragm of the subject; (b) for an esophageal segment, determine and display a first number indicative of a first distance from the coil to the detector device; (c) for a stomach segment, determine and display a second number termine and display a third number indicative of a third distance from the coil to the indicative of a second distance from the coil to the detector device; and (d) for a pylorus segment, de detector device; and (e) for a duodenum segment, determine and display a fourth number indicative of a fourth distance from the coil to the detector device.

In another embodiment, the instructions, when executed by the processor, cause the processor to, in cooperation with the detector device, the coil and the memory device, while the coil is being advanced or removed from the NGT, record a route through the subject body. In another embodiment, the route includes an X-Y location. In another embodiment, the first predetermined line and the second predetermined line intersect at a point representative of a xiphoid sternal junction of the subject. In another embodiment, the coil is configured to transmit electromagnetic signals. In another embodiment, the system component for monitoring the location of the NGT includes a plurality of wires having an end portion which is connected to the coil, the plurality of wires being at least one of a stylet and a guide wire. In another embodiment, the detector device includes a plurality of receiving coils which receive electromagnetic signals from the coil. In another embodiment, the instructions, when executed by the processor, cause the processor to, in cooperation with the display device, the detector device, the coil and the memory device, while the coil is being advanced or removed from the NGT, generate and display arrow symbols which are indicative of a direction of travel of the coil. In another embodiment, the instructions, when executed by the processor, cause the processor to, in cooperation with the display device, the detector device, the coil and the memory device, while the coil is being advanced or removed from the NGT, for a jejunum segment, determine and display a fifth number indicative of a fifth distance from the coil to the detector device.

In another embodiment, the nasogastric tube comprises a wire having an end portion which is connected to the nasogastric or enteral location element, the of wire being at least one of a stylet, a guide wire, or both. In another embodiment, the nasogastric tube comprises a plurality of wires having an end portion which is connected to the nasogastric or enteral location element, the plurality of wires being at least one of a stylet, a guide wire, or both.

As will be described in more detail hereinbelow, the nasogastric location element, the suction mechanism and the gastric decompression mechanism are, in some embodiments, disposed (situated) and associated by one or more same lumens. In other embodiments, a nasogastric location element, the suction mechanism and the gastric decompression mechanism are configured to perform by independent lumens.

According to some embodiments, the NGT is composed of at least one main lumen and a plurality of peripheral lumens, wherein a portion of said plurality of peripheral lumens comprise at least one gastric decompression port and a portion of said plurality of peripheral lumens comprise at least one suction port configured to sealingly draw an inner wall of an esophagus thereagainst.

According to additional embodiments, the NGT is composed of at least one main lumen, one or more lumens comprising a nasogastric location element and at least one gastric decompression port and one or more peripheral lumens comprising at least one suction port configured to sealingly draw an inner wall of an esophagus thereagainst.

Furthermore, the structure of an NGT, according to some embodiments of the present invention, enables locally positioning selective application of the vacuum within the esophagus. Thus, the location of the esophagus coupling to the tube may be changed in time in order to diminish tissue damage to the esophagus.

According to some embodiments, the peripheral (vacuum) lumens are configured to aspirate fluids such as gastric reflux from the esophagus and/or house a nasogastric location element. In some embodiments, said at least one suction port is configured to aspirate fluids from the esophagus. By virtue of applying vacuum to the peripheral lumens of the NGT described herein, the at least one suction port is used for sealingly drawing an inner wall of an esophagus thereagainst and interchangeably or simultaneously aspirate fluids from the esophagus. One skilled in the art will is well capable of determining the vacuum pressure to be applied for sealing the esophagus and/or aspirating fluids from the esophagus.

An NGT according to the present invention can be used in ICU, or elsewhere, in order to reduce the complications associated with reflux such as the risk of VAP and in order to prevent or reduce tissue damage.

According to the present invention, the inner wall of the esophagus is drawn by negative pressure (vacuum) towards and against the outer contour of the NGT. A vacuum control unit, which is connected to the hospital vacuum unit or any other vacuum unit, enables either simultaneous vacuum pressure in one or more suction units of the NGT or changeable vacuum pressure between the different suction units. In this way, the NGT of the present invention prevents reflux and aspiration of substances or liquids into the patient's lungs and prevents tissue damage, while obviating the need to remove and replace the entire device from the patient's esophagus.

In some embodiments, a tube according to the present invention may be used in other locations in the GI tract or in any other body lumen, such as arteries, veins, etc. However, for simplicity of discussion, this tube is referred to throughout the specification as an NGT.

Reference is now made to FIGS. 1 and 2, which illustrate a nasogastric tube 10, constructed and operative in accordance with a non-limiting embodiment of the present invention.

NGT 10 includes a main (typically, but not necessarily, central) lumen 12. Main lumen 12 may be used to feed and administer drugs and other oral agents, and may also be used for sucking fluids from the stomach. As such, as is known in the art, main lumen 12 may be a double lumen, one lumen for feeding and the other lumen for suction (not to be confused with the vacuum lumens mentioned later). Main lumen 12 is provided with one or more suitable proximal connectors 14 for connecting to a source of substances for feeding or administering, and optionally to a source of pressure (e.g., suction), as is known in the art.

NGT 10 includes one or more vacuum lumens 16 that peripherally surround main lumen 12. The term "peripherally surround" as used in the description and claims, encompasses continuous surrounding (no gaps between the vacuum lumens or one continuous, peripheral vacuum lumen) and discontinuous surrounding (wherein there are separations between discrete vacuum lumens). In one embodiment, illustrated in FIG. 2, there are four vacuum lumens 16 peripherally spaced around main lumen 12; the invention is not limited to this number of vacuum lumens. The vacuum lumens 16 may be equally or unequally spaced from each other. Main lumen 12 and vacuum lumens 16 are thus arranged as concentrically arranged conduits. Vacuum lumens 16 are coupled with a vacuum source 18, such as via a pressure regulator 20 and a valve 22, which form a vacuum control unit.

Main lumen 12 may be constructed from any suitable biocompatible material, such as but not limited to, polyurethane, silicone, polyvinyl chloride and many others. The vacuum lumens 16 may be constructed of similar materials, but alternatively may be constructed of medically safe metals, such as but not limited to, stainless steel, titanium alloys, NITINOL and others. Generally, without limitation, main lumen 12 may have a length in the range of 50 to 150 cm, with an outside diameter in the range of 5-12 Fr.

Main lumen 12 and vacuum lumens 16 may be constructed as one unit. Alternatively, vacuum lumens 16 may form a separate unit which is slid over main lumen 12 after insertion of main lumen 12 into the patient body. As another alternative, vacuum lumens 16 may be first introduced into the patient, and main lumen 12 may be slid in between vacuum lumens 16.

With reference to FIG. 1, vacuum lumen 16 may include a vacuum sealing portion 24, which may include one or more suction ports 26 and possibly a nasogastric location element. As shown in FIG. 1, some vacuum lumens 16 may have more suction ports than others. As shown in FIG. 3, upon application of vacuum generated by vacuum source 18, the inner wall of the esophagus is drawn by negative pressure towards and against suction ports 26 (the outer contour of NGT 10). The outer contour of NGT 10, at least at vacuum sealing portion 24, is preferably round (circular or oval), for better conforming to and sealing of the esophagus. In one embodiment, the vacuum sealing restricts at least 60% of the passage through the esophagus.

Pressure regulator 20 may be used to reduce or otherwise regulate the negative pressure generated by vacuum source 18. For example, pressure regulator 20 may be used to match the vacuum level generated by vacuum source 18 to the vacuum level needed in vacuum sealing portion 24. Such vacuum pressure may be, for example, between 0.5-50, 50-100, 100-200, 200-300, 300-400, 400-500, 500-600 or 600-760 mmHg. Different vacuum pressure values may be suitable to different patients and/or to different luminal structures into which the tube of the present invention is inserted. Furthermore, vacuum lumen 16 includes a gastric decompression port as will be described in more detail hereinbelow. In some embodiments, vacuum lumen 16 including a gastric decompression port 23 also includes one or more suction ports 26, or alternatively is devoid of suction ports 26. Upon application of vacuum generated by vacuum source 18, a subject's abdomen (e.g., stomach and/or intestines) is decompressed to remove gastric gas, excessive reflux or the like. Pressure regulator 20 may apply vacuum pressure, for example, between 0.5-50, 50-100, 100-200, 200-300, 300-400, 400-500, 500-600 or 600-760 mmHg, required for gastric decompression. Those of skill in the art will recognize that the required vacuum pressure may be dependent on the amount of gas and/or excessive reflux being decomposed, as well as whether the vacuum pressure is applied in a constant or pulse manner. Valve 22 may provide variability to the applied vacuum pressure to vacuum lumen 16 which includes decompression port 23. Valve 22 may be used to shift the vacuum between the different vacuum lumens 16 so that the suction level is not constant over time in the vacuum sealing portion 24, which may provide variability in how the esophagus wall is sucked in, and for how long.

NGT 10 may be provided with different numbers of vacuum sealing portions 24 and suction ports 26, and the vacuum to the sealing portions 24 may be regulated so as to create peristaltic movement or other oscillatory movement of the esophagus.

In accordance with an embodiment of the invention, one or more auxiliary suction ports 33 are provided proximal to vacuum sealing portion 24. Since vacuum sealing portion 24 seals off the esophagus, any oropharyngeal secretions, such as saliva, may accumulate above (i.e., proximal to) vacuum sealing portion 24. Auxiliary suction ports 33 may be used to suck and remove such secretions. Additionally or alternatively, one or more of vacuum lumens 16 may be used to evacuate liquids arriving from the patient's stomach. That is, if a reflux occurs, one or more of vacuum lumens 16 may withdrawn at least a portion of it, through decompression port(s) 23 and/or suction ports 26, towards valve 22. There, the stomach contents may be collected inside a suitable reservoir and then discarded.

Vacuum source 18 is preferably activated following the insertion and localization of NGT 10 in the esophagus in order to reduce the risk of VAP, or other bacterial infections, by preventing or minimizing reflux food and liquid aspiration into the lungs.

One method of using NGT of the present invention includes the following steps, without limitation and not necessarily in sequential order:
a) introducing NGT into the esophagus of the subject;
b) Positioning and/or localizing NGT in-situ;
c) applying vacuum to one or more of the vacuum sealing portion(s);
d) adjusting the vacuum level (which may be done before step a);
e) after achieving a desired sealing of the esophagus wall to NGT 10, changing the vacuum intervals between the vacuum lumens 16, manually or automatically, such that NGT remains intact to the esophagus; and
(f) applying, manually or automatically, vacuum to one or more of vacuum lumen 16 which include decompression port(s) 23.

Reference is now made to FIGS. 4A, 4B and 4C. FIG. 4A is a simplified, schematic illustration of a transparent front view of a portion of a nasogastric tube 50, constructed and operative in accordance with another non-limiting embodiment of the present invention. FIG. 4B is a simplified schematic illustration of a cross-section along line I-I of nasogastric tube 50 of FIG. 4A. FIG. 4C is a simplified schematic illustration of a cross-section along line II-II of nasogastric tube 50 of FIG. 4A. Nasogastric tube 50 is generally similar to nasogastric tube 10 of FIG. 1. The differences between nasogastric tube 10 and nasogastric tube 50 are detailed herein below. FIG. 4A shows a proximal portion of nasogastric tube 50 to be inserted into a patient's esophagus and with respect to it. Nasogastric tube 50 includes an additional upper portion, which is not shown, that is left outside of the patient's body and is coupled with, for example, vacuum source 18, pressure regulator 20 or valve 22. Nasogastric tube 50 includes main lumen 12 and six vacuum lumens 16, specifically denoted 16a, 16b, 16c, 16d, 16e and 16f. However, in other embodiments (not shown), a different number of vacuum lumens, such as four or more, may be used. Nasogastric tube 50 further includes a decompression port(s) 23 located distal to the longitudinal location of suction ports 26b, and 26f, as shown in FIG. 4A. Decompression port(s) 23 are, in some embodiments, configured to be positioned inside a stomach or a duodenum.

Each vacuum lumen 16 includes a suction port 26, specifically denoted 26a, 26b, 26c, 26d, 26e and 26f correspondingly. Therefore, each of suction ports 26 is associated with one of lumens 16. Suction ports 26a, 26b, 26c, 26d, 26e and 26f are distributed along a longitudinal axis of nasogastric tube 50. Suction ports 26a, 26c and 26e are located above suction ports 26b, 26d and 26f along the longitudinal axis of nasogastric tube 50 and with respect to a patient's body. Such a longitudinal axis may be advantageously located within main lumen 12.

With specific reference to FIGS. 4B and 4C, FIG. 4B shows a cross-section of suction ports 26a, 26c and 26e. Suction ports 26a, 26c and 26e are peripherally distributed around main lumen 12 in the same longitudinal location with respect to main lumen 12 (i.e., along a longitudinal axis of nasogastric tube 50). FIG. 4C shows a cross-section of suction ports 26b, 26d and 26f. Suction ports 26b, 26d and 26f are peripherally distributed around main lumen 12 in the same longitudinal location with respect to main lumen 12, as shown in FIG. 4A. The longitudinal location of suction ports 26a, 26c and 26e is different from and located above the longitudinal location of suction ports 26b, 26d and 26f, as shown in FIG. 4A. Generally, without limitation, the distance between suction ports 26a, 26c and 26e and 26b, 26d and 26f is in the range of 50 to 250 mm, or 100 to 150 mm.

Therefore, for example, applying vacuum to vacuum lumens 16a or 16c or 16e or to any combination thereof, allows sealing of the esophagus against nasogastric tube 50 in different peripheral locations (i.e., depending on the vacuum lumens which are used) and in different levels (i.e., depending on how many vacuum lumen are used) but in a specific longitudinal location (denoted by line I-I with respect to nasogastric tube 50 in FIG. 4A). In order to allow maximal sealing of the esophagus, vacuum may be applied to vacuum lumens 16a, 16c and 16e together at the same time. Applying vacuum to vacuum lumens 16b or 16d or 16f or to a combination thereof, would result the same correspondingly but in different peripheral locations with respect to main lumen 12 (i.e., according to the peripheral locations of vacuum lumens 16b, 16d or 16f) and in particular, in a different longitudinal location along nasogastric tube 50, denoted by line II-II in FIG. 4A. Vacuum may be also applied to vacuum lumens located in different longitudinal locations along nasogastric tube 50 at the same time.

Hence, the location of the vacuum lumens within the nasogastric tube according to the present invention determines the peripheral location of the applied vacuum and the location of the suction ports determines the longitudinal location of the applied vacuum within the esophagus. It should be noted that the positioning of nasogastric tube 50 within the esophagus as performed by the attending caregiver should be also considered. Switching the applied vacuum between the vacuum lumens allows applying vacuum on the esophagus inner wall at different locations peripherally and longitudinally during time, thus diminishing or preventing damage to the esophagus tissue facing the suction ports.

Valve 22 may be used to switch the vacuum between one or more vacuum lumens 16. Valve 22 may be separately connected to each vacuum lumen 16 or, for example, connected to all of vacuum lumens 16 having suction ports 26 at the same longitudinal location with respect to nasogastric tube 50 together. Obviously, the latter setup of valve 22 allows less freedom in switching between vacuum lumens 16. Hence, valve 22 may be used to switch the applied vacuum after a time duration from one or more vacuum lumens located at specific peripheral and longitudinal locations to one or more vacuum lumens located at other peripheral locations or furthermore at other longitudinal locations. Such a switch may be preformed gradually in order to keep the esophagus sealed at least to some extent against nasogastric tube 50 during the switch.

Nasogastric tube 50 may include two or more vacuum lumens 16 which peripherally surround main lumen 12. At least two of vacuum ports 26 are located at different longitudinal locations along nasogastric tube 50 in order to allow a longitudinal location switch within the esophagus.

Suction ports 26 are elliptical but may be of any other form, such as circular. Suction ports 26 may include a graduated edging 28 to prevent or diminish damage to the esophagus tissue while an inner wall of the esophagus is pressed against suction ports 26. Graduated edging 28 is advantageously graduated in an obtuse angle. Graduated edging 28 may be graduated entirely or only include a graduated portion. Generally, graduated edging 28 may provide each of suction ports 26 with a concave shape, having an opening approximately in its middle.

Nasogastric tube 50 may be coupled with a manifold (not shown). The manifold may connect vacuum lumens 16 to valve 22 in a separate manner to allow vacuum application to one or more vacuum lumens 16. The manifold may be transparent in order to visually monitor backflow of gastric substances, such as bile.

In some embodiments, at least one suction port 26 may include two or more suction ports, successively arranged along a portion of a longitudinal axis of nasogastric tube 50.

Reference is now made to FIGS. 7A and 7B. FIG. 7A illustrates a simplified, schematic illustration of a portion of an NGT 10, constructed and operative in accordance with a non-limiting embodiment of the present invention. FIG. 7B is a simplified and enlarged illustration of a distal portion of the NGT comprising one or more gastric decompression ports. NGT 10 includes, for example, a vacuum sealing portion 24 comprising two suction ports 28 and 26 distributed between two different locations along the length of NGT 10. NGT 10 further includes one or more gastric decompression ports 23a and 23b disposed distally to the vacuum sealing portion 24. Typically, the one or more gastric decompression ports 23a and 23b are configured to be positioned inside a stomach and/or a proximal duodenum.

Generally, without limitation, the distance between one or more gastric decompression ports 23 to at least one suction port is in the range of 50 to 200 mm.

The one or more gastric decompression port(s) 23 is associated with at least one of vacuum lumen 16 (not shown). In some embodiments, the one or more gastric decompression port(s) 23 is associated with a vacuum lumen 16 which comprises one or more suction ports 26. In other embodiments, the one or more gastric decompression port(s) 23 is associated with at least one additional vacuum lumen 16 (such as a vacuum lumen 16 devoid of suction ports 26). Gastric decompression port(s) 23 may be configured to be positioned inside a stomach. Gastric decompression port(s) 23, in another embodiment, may be configured to be positioned inside a proximal duodenum. Gastric decompression port 23 is, in some embodiments, disposed distally to vacuum sealing portion 24 (and suction ports 28 and 26). Decompression port(s) 23 may be elliptical or of any other form, such as circular.

NGT 10 further includes one or more feeding port 25 at the distal end of main lumen 12. In additional embodiments, such as for simultaneous feeding and decompression, the one or more feeding ports 25 are distal to the one or more gastric decompression ports 23. Feeding port 25 may be configured to be positioned in the stomach or in the duodenum. Generally, without limitation, the distance between one or more gastric decompression ports 23 to at least one feeding port is in the range of 50 to 300 mm, or in the range of 100 to 200 mm.

In one embodiment, the one or more gastric decompression port(s) 23 are configured to be positioned in a position selected from a distal esophagus (i.e., distal to vacuum sealing portion 24), inside a stomach, proximal duodenum, or a combination thereof. In embodiments wherein gastric decompression port(s) 23 are configured to be positioned in the proximal duodenum, feeding port 25 may be configured to be positioned in a distal duodenum.

Vacuum lumen 16 comprising a decompression port 23 may be constructed of similar materials to vacuum lumen 16 comprising suction ports 26, but alternatively may be constructed of medically safe metals, such as but not limited to, stainless steel, titanium alloys, NITINOL and others.

As known to one skilled in the art, the system described herein may further comprise a guiding probe (e.g., a stylet) for inserting the NGT to a subject. Said guiding probe is typically is removed after confirming the correct placement of the NGT.

A method of using NGT 50 of the present invention may include the following steps, without limitation and not necessarily in sequential order:

a) introducing the NGT into an esophagus of a patient;
   b) applying vacuum to one or more decompression ports; and
   c) applying vacuum to one or more suction ports interchangeably between the differently located suction ports so as to sealingly draw an inner wall of the esophagus thereagainst each time in a different location along the esophagus.

The vacuum may be applied to vacuum lumen(s) comprising one or more decompression ports in a constant manner or alternatively in timely intervals. As such, vacuum may be applied to the decompression ports prior to, during or after a patient is being fed by the NGT described herein. In additional embodiments, vacuum may be applied to the decompression ports according to the subject request, such as in result to abdominal discomfort, including but not limited to, excessive gastric gas or the like.

The vacuum may be applied to one or more vacuum lumens each time, and in each time to vacuum lumens which include suction ports peripherally distributed around the same location along a longitudinal axis of the NGT (for example, vacuum lumens 16a and 16c or vacuum lumens 16b, 16d and 16f of FIGS. 4A, 4B and 4C) or peripherally distributed around different locations along a longitudinal axis of the NGT (for example, vacuum lumens 16a and 16d of FIGS. 4A, 4B and 4C).

The interchanging between the vacuum lumens to which a vacuum is applied may be performed at various manners, for example, it may be performed once or more per patient while each location change may be performed once in a constant or variable period of time, all according to the caregiver discretion regarding the specific patient.

The method may further include the step of regulating the vacuum so that a suction level is not constant over time in the suction ports. The vacuum may be regulated to the vacuum ports so as to create peristaltic movement or other oscillatory movement of the esophagus.

In some embodiments, the vacuum may be applied such that to restricts at least 60% of passage through the esophagus.

The method may further include the step of visually monitoring a transparent manifold which couples the vacuum lumens with a valve for backflow of gastric substances, such as bile.

In some embodiments of the present invention, the present invention may be utilized to insert a nasogastric location element through main lumen 12, through one or more of vacuum lumens 16 and/or through a different, dedicated lumen (not shown) into the patient's body. Such a nasogastric location element or probes may include, for example: a temperature sensor, an electromagnetic radiation sensor, a pH sensor, an image sensor, a fiber optic, an ultrasound probe, an OCT (optical coherence tomography) probe, a mini MRI (magnetic resonance imaging) probe, etc.

Reference is now made to FIG. 6, which shows a cross section of a nasogastric tube 200, optionally similar to tube 10 (FIGS. 1-2) and/or to tube 50 (FIGS. 4A-4C). For simplicity of illustration, the cross section is shown at a portion of the tube which lacks any suction ports.

Tube 200 may include one or more radiopaque stripes, such as stripes 202-212, disposed along the longitudinal axis of the tube. Radiopaque stripes 202-212 may be visible, when tube 200 (or a portion thereof) is inside the patient, using X-ray imaging and/or other types of electromagnetic radiation imaging. That is, radiopaque stripes 202-212 are made of a radiodense material which inhibits the passage of some or all electromagnetic radiation, thereby creating a contrast in relation to more radiolucent body tissue and/or radiolucent portions of a medical device. Generally, if two or more parallel, longitudinal radiopaque stripes are present, the resulting electromagnetic radiation image may enable a better depth perception of the tube. This, since one or more of the stripes may be farther away from the imager than other one or more of the stripes. Furthermore, having two or more parallel, longitudinal radiopaque stripes may enable visualizing a situation in which the tube is twisted; this will result in a spiral-like image of the stripes.

An example of a suitable radiopaque material is Barium sulfate, but those of skill in the art will recognize that other known radiodense materials may be used. In case Barium sulfate is used, its density in stripes 202-212 may be, for example, between 40-60%, between 60-80% or higher. The remainder percentage may be one or more filler materials.

Stripes 202-212, whether by virtue of their high-percentage Barium sulfate contents and/or their thickness, may endow tube 200 with a certain rigidity. This rigidity is to a degree which assists the caregiver in pushing the tube down the GI tract (or any other bodily lumen) on one hand, but still allows the tube to resiliently maneuver through the pertinent bodily lumen.

Optionally, one or more of stripes 202-212 may have an essentially triangular cross section, as shown in the figure. One apex of the triangle may be directed towards the inside of tube, and the base opposite to that apex may be directed towards the outside of the tube. In other embodiments (not shown), one or more of the stripes may have a rectangular cross-section, a circular cross-section, or an otherwise shaped cross-section.

Stripes 202-212 are optionally embedded, at least partially, in the outer wall of tube 200. Further optionally, stripes 202-212 may slightly protrude beyond the outside surface of the tube. For example, the protrusion may be by 50-100 micrometers, 100-150 micrometers, 150-250 micrometers, 250-400 micrometers or more. This protrusion may enable the caregiver holding tube 200 to get a better grip of the tube, especially when the tube has to be rotated. The protrusion may prevent the tube from slipping in the caregiver's hands while rotated.

In another embodiment, a NGT comprises at least one nasogastric location element. In another embodiment, a NGT comprises at least one nasogastric location element situated within a peripheral lumen which is a vacuum lumen. In another embodiment, a NGT comprises at least one nasogastric location element situated within a peripheral lumen which is not a vacuum lumen. In another embodiment, a NGT comprises at least one nasogastric location element situated within a peripheral lumen, wherein the peripheral lumen housing nasogastric location element is sealed at its proximal end. In another embodiment, a NGT comprises at least one nasogastric location element situated within a peripheral lumen, wherein the peripheral lumen housing nasogastric location element is sealed at its distal end. In another embodiment, a NGT comprises at least one nasogastric location element situated within a peripheral lumen, wherein the peripheral lumen housing nasogastric location element is sealed at both the proximal end and the distal end. In some embodiments, said main lumen comprises at least one feeding port at or adjacent to the distal end of said nasogastric tube, at least one nasogastric location element, or a combination thereof. In some embodiments, said main lumen comprises at least one feeding port at or adjacent to the distal end of said nasogastric tube.

Figure 8B:
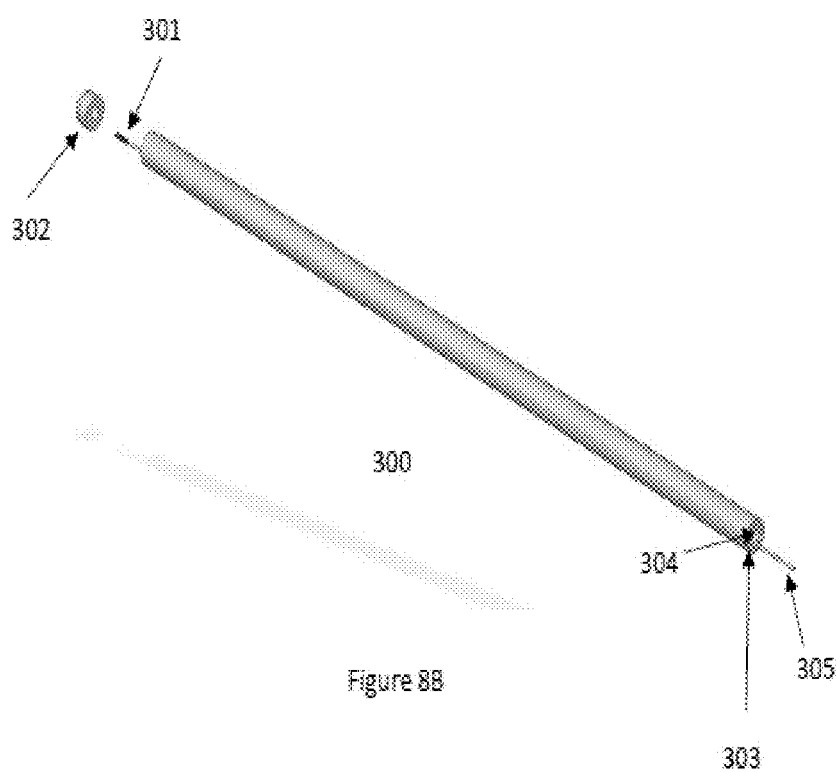

Reference is now made to FIG. 8, which shows the nasogastric location element 301 situated within a peripheral lumen 303 (surrounding main lumen 304) and possibly protruding from the NGT 300. The peripheral lumen 303 in FIG. 8 is free of suction ports and its walls are continuous. The peripheral lumen 303 may be sealed at its proximal end (8A) or at its distal end (8B). Sealing by cup 302 provides physical protection to the nasogastric location element 301. Wires 305 are connected to the nasogastric location element 301.

As used herein "adjacent to the distal end of said nasogastric tube" refers to at most 10 cm, at most 9 cm, at most 8 cm, at most 7 cm, at most 6 cm, at most 5 cm, at most 4 cm, at most 3 cm, at most 2 cm, at most 1 cm, at most 0.75 cm, at most 0.5 cm, at most 0.25 cm from the distal end of said nasogastric tube. Each possibility is a separate embodiment of the present invention.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:

1. A nasogastric tube having a length and comprising:
   (a) a main lumen having one or more proximal connectors configured to connect to a source of substances or pressure;
   (b) at least four vacuum lumens peripherally circumferentially surrounding said main lumen;
   (c) at least four suction ports configured to circumferentially and sealingly draw an inner wall of an esophagus thereagainst, each of said at least four suction ports associated with a different one of said at least four vacuum lumens, wherein said at least four suction ports are distributed between at least two different locations along a longitudinal axis of said nasogastric tube;
   (d) a valve connected to said at least four vacuum lumens, said valve configured to shift an applied vacuum between different ones of said at least four vacuum lumens, thereby: varying how said inner wall of the esophagus is circumferentially and sealingly drawn, and changing vacuum intervals between said different ones of said at least four vacuum lumens; and
   (e) at least one nasogastric location element contained within said nasogastric tube.

2. The nasogastric tube of claim 1, further comprising at least one gastric decompression port associated with at least one of said at least four vacuum lumens, said at least one gastric decompression port being disposed distally to the at least two different locations along a length of said nasogastric tube.

3. The nasogastric tube of claim 1, wherein said at least one nasogastric location element contained within said nasogastric tube is contained within an additional dedicated outer lumen peripheral to the main lumen.

4. The nasogastric tube of claim 3, wherein said additional dedicated outer lumen is sealed at both a proximal end and a distal end.

5. The nasogastric tube of claim 1, wherein said at least one nasogastric location element contained within said nasogastric tube is contained within a wall of said at least four vacuum lumens, a wall of said main lumen, or a combination thereof.

6. A system comprising the nasogastric tube of claim 1 and a feeding source, a suction source or a combination thereof.

7. The nasogastric tube of claim 1, further comprising a feeding mechanism and a suction mechanism, said feeding mechanism comprised of said main lumen and having one or more proximal connectors configured to connect to a source of substances or pressure, and wherein said suction mechanism and/or a gastric decompression mechanism comprised of at least one vacuum lumen of said at least four vacuum lumens.

8. The nasogastric tube according to claim 1, wherein said main lumen and said at least four vacuum lumens are constructed as one unit.

9. The nasogastric tube according to claim 1, wherein said at least four vacuum lumens are a separate unit from said main lumen, and wherein said at least four vacuum lumens are slidable relative to said main lumen.

10. The nasogastric tube according to claim 1, wherein said main lumen and said at least four vacuum lumens are arranged as concentrically arranged conduits.

11. The nasogastric tube according to claim 1, further comprising one or more auxiliary suction ports proximal to said at least four suction ports.

12. The nasogastric tube according to claim 1, wherein each of said at least four suction ports comprises a graduated edging.

13. The nasogastric tube of claim 1, further comprising a manifold configured to connect said at least four vacuum lumens to said valve.

14. The nasogastric tube of claim 13, wherein said manifold is transparent.

15. The nasogastric tube of claim 1, wherein said at least four vacuum lumens comprise more than four vacuum lumens.

16. The system according to claim 1, wherein said nasogastric tube further comprises two or more longitudinal radiopaque stripes.

17. The nasogastric tube according to claim 16, wherein said two or more longitudinal radiopaque stripes are embedded in an outer wall of said nasogastric tube.

18. The nasogastric tube according to claim 1, wherein said nasogastric location element is an electro magnet.

* * * * *